United States Patent [19]

Ito et al.

[11] Patent Number: 5,408,093
[45] Date of Patent: Apr. 18, 1995

[54] OPTICAL COMPUTED TOMOGRAPHY EQUIPMENT HAVING IMAGE INVERTING OPTICAL DEVICE

[75] Inventors: Yoshitoshi Ito, Ome; Fumio Kawaguchi, Hinode; Yuichi Yamashita; Atsushi Maki, both of Hachioji, all of Japan

[73] Assignee: Hitachi, Ltd., Tokyo, Japan

[21] Appl. No.: 204,370

[22] PCT Filed: Aug. 30, 1993

[86] PCT No.: PCT/JP93/01220

§ 371 Date: Mar. 11, 1994

§ 102(e) Date: Mar. 11, 1994

[87] PCT Pub. No.: WO94/05209

PCT Pub. Date: Mar. 17, 1994

[30] Foreign Application Priority Data

Aug. 31, 1992 [JP] Japan .................................. 4-230926

[51] Int. Cl.⁶ .................... G02B 5/04; G02B 6/00; A61B 6/03
[52] U.S. Cl. .................... 250/227.26; 128/633; 250/341.1
[58] Field of Search ........... 250/227.20, 227.24, 250/227.26, 339.06, 341, 358.1; 356/73.1; 128/633, 634, 664, 665, 666

[56] References Cited

U.S. PATENT DOCUMENTS

| | | | |
|---|---|---|---|
| 3,602,640 | 8/1971 | Maillet et al. | 250/227.26 |
| 4,512,036 | 4/1985 | Laor | 250/227.26 |
| 4,910,404 | 3/1990 | Cho et al. | 250/341 |
| 5,349,951 | 9/1994 | Ito et al. | 128/633 |

FOREIGN PATENT DOCUMENTS

| | | |
|---|---|---|
| 72542 | 4/1985 | Japan . |
| 276000 | 12/1986 | Japan . |
| 115548 | 5/1988 | Japan . |
| 56411 | 3/1989 | Japan . |

OTHER PUBLICATIONS

Hecht et al., *Optics*, Addison-Weseley Publishing Co., Inc., 1974, p. 133.

*Primary Examiner*—David C. Nelms
*Assistant Examiner*—John R. Lee
*Attorney, Agent, or Firm*—Antonelli, Terry, Stout & Kraus

[57] ABSTRACT

Optical computed tomography equipment adapted to speed up the scanning of a subject under test using irradiated light so as to shorten the measuring time involved. The light from a light source (15-1, 15-2) is guided over an optical fiber thread (12-5c) to an image inverting optical system comprising a dovetail prism (13-1) and two lenses (14-2, 14-1). Past the optical system, the light enters one of the threads making up an optical fiber (12-1). As the dovetail prism (13-1) is rotated around its optical axis, the light from the optical fiber thread (12-5c) consecutively enters different threads of the optical fiber (12-1), causing the irradiation position to scan a subject (11) of the test. The incident light, having passed through the subject (11) in various directions, goes through the respective threads of the optical fiber (12-1) to reach the image inverting optical device. From there, the light enters the corresponding threads of an optical fiber (12-4) and is detected by photo detectors (16-2a, 16-2b, etc.).

9 Claims, 6 Drawing Sheets

OPTICAL COMPUTED TOMOGRAPHY EQUIPMENT HAVING IMAGE INVERTING OPTICAL DEVICE

TECHNICAL FIELD

The present invention relates to improved optical computed tomography equipment. More particularly, the invention relates to an improved method for irradiating light to a test subject.

BACKGROUND ART

Computed tomography (CT) equipment has gained widespread acceptance as medical equipment. The CT equipment comes in various types: X-ray CT, nuclear magnetic resonance (NMR) CT, positron CT and ultrasonic wave CT. The most recent version of the equipment is optical CT equipment that utilizes visible or near infrared light.

The optical CT equipment operates on the so-called back projection method for image reconstitution. To use this method requires procuring projection data which is obtained as follows: a light beam is first irradiated to various points on the test subject to measure the intensity of the transmitted light from the subject in diverse directions. The measurements are used to find the light transmittance of the subject at the respective irradiation points. To acquire the projection data further involves having the irradiation position of light scan a number of points along the periphery of the subject under test; at each of the irradiation points, the light transmittance of the subject must be measured in various directions.

Figure 2:
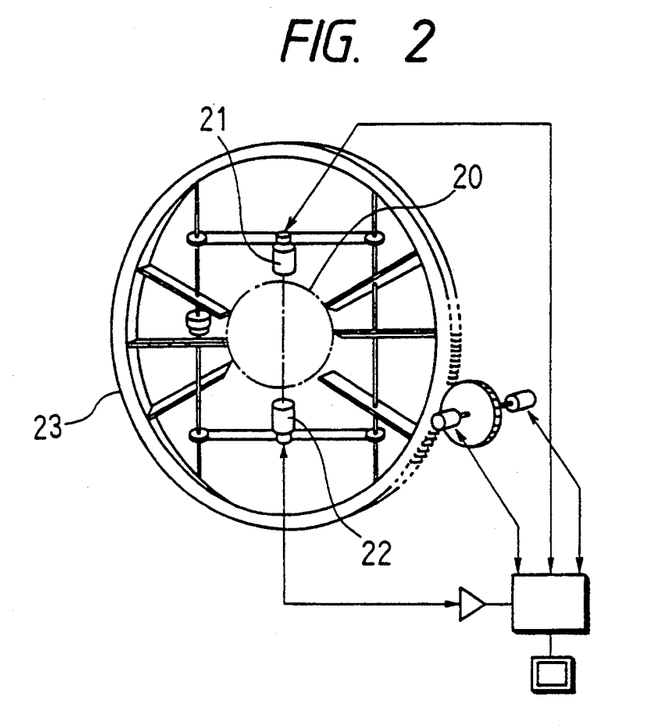
FIG. 2 is a schematic view of conventional optical CT equipment.
Figure 3:
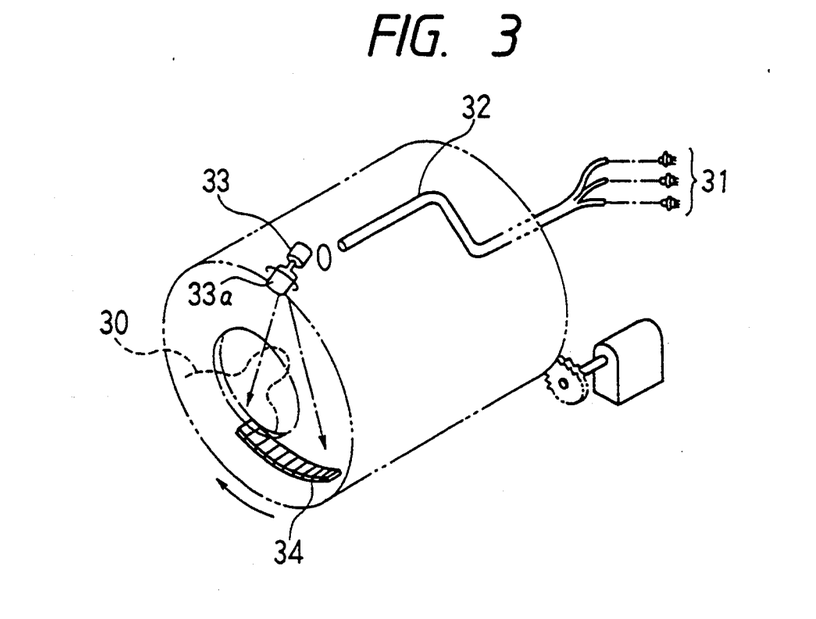
FIG. 3 is a schematic view of another conventional optical CT equipment.

The conventional scanning methods for irradiating the light beam to the test subject are typically shown in FIGS. 2 and 3. The method of FIG. 2 is disclosed in Japanese Patent Laid-Open No. 115548/1988. This method involves retaining a light source 21 and a photo detector 22 within the same gantry 23 that is rotated around the test subject 20. The rotation of the gantry 23 changes the irradiation position of light and the detecting position of the transmitted light. The method of FIG. 3 is disclosed in Japanese Patent Laid-Open No. 56411/1989. According to this method, a light beam guided from the light source 31 via an optical fiber 32 is made to scan a test subject 30. The scanning is accomplished by use of an optical scanner 33 comprising a wobbling mirror 33a. The light transmitted through the subject 30 is detected by a photo detector array 34 having numerous photo detectors arranged therein. The individual photo detectors in the photo detector array 34 are switched electrically to vary that point on the subject at which to measure the transmitted light.

Figure 4:
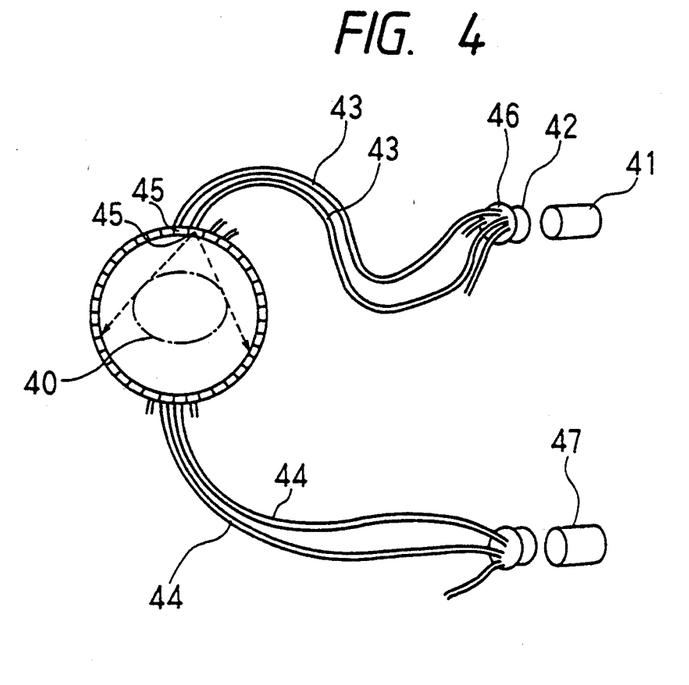
FIG. 4 is a schematic view of another conventional optical CT equipment.

Another conventional method is illustrated in FIG. 4. This method, disclosed in Japanese Patent Laid-Open No. 72542/1985, employs optical fibers 43 and 44 in switching between two positions: irradiation position on the test subject 40, and measuring position of the transmitted light from the subject 40. One disadvantage of the methods in FIGS. 2 and 3 is, as illustrated, their bulky equipment attributable to the relatively large mechanics required. The method of FIG. 4 is an attempt to bypass that disadvantage using optical fibers.

Without direct relevance to the optical CT, there exists a conventional technique for consecutively monitoring a plurality of measuring points. This technique, disclosed in Japanese Patent Laid-Open No. 276000/1986, utilizes light for transmission of information from the sensors at the measuring points to a central monitoring unit. The technique also uses an optical system comprising optical fibers and a dovetail prism arrangement for switching between the transmission and the reception of light to and from the sensors and the central monitoring unit.

The method of FIG. 4 appears to have resolved one of the disadvantages of the prior art in that it simplifies the mechanics through the use of optical fibers. In fact, the method has created a number of new problems. One such problem is that the method has low efficiency in utilizing the light coming from a light source 41. The reason for the reduced efficiency is as follows: the thread ends on one side of an optical fiber 43 are located in individual irradiation positions 45 oriented toward the test subject 40, and the thread ends on the other side of the optical fiber 43 are arranged in a circular manner on a fiber holder 46. The light source 41 is placed in front of the fiber holder 46. The light from the light source 41 is made incident on the optical fiber 43 so that the light will be expanded for irradiation onto the entire surface of the holder 46. At this point, a rotary disk 42 having a single hole therethrough is placed before the fiber holder 46. Rotating the rotary disk 42 allows the light to go through the hole into each of the optical fiber threads successively. Only the light having passed through the hole enters the optical fiber 43. This scheme of consecutively switching the irradiation position over the test subject 40 has the disadvantage of getting the rotary disc 42 to block most of the light coming from the light source 41; only a limited part of all light from the light source 41 is utilized for irradiation to the subject 40. This means that to obtain a sufficient quantity of light for actual measurement requires furnishing a light source of a very large output.

Another disadvantage of the method of FIG. 4 is as follows: the use of a single photo detector 47 entails a very wide range of the intensity of the light that is incident on the detector. That is, the photo detector 47 must be one having an extensive dynamic range. The method of FIG. 4 involves having the single photo detector 47 detect on a time series the light transmitted through various measuring points on the periphery of the subject 40 via the optical fiber 44. The quantity of the transmitted light varies considerably from one measuring point to another; the variation in light intensity can span several orders of magnitude. The photo detector 47 thus needs to be one that is expensive and provides a dynamic range addressing several orders of magnitude.

DISCLOSURE OF INVENTION

It is therefore an object of the present invention to provide optical computed tomography (CT) equipment that is small and inexpensive.

It is another object of the invention to provide a light irradiation method for irradiating efficiently the light from a light source onto the test subject.

In carrying out the invention and according to one aspect thereof, there is provided an optical CT equipment having a plurality of threads of optical fiber through which the light from a visible or near infrared light source is guided toward the periphery of the subject to be tested, the transmitted light through the subject being guided through the same threads of optical fiber to a photo detector for measurement. Halfway through the optical fiber is interposed an optical system comprising an optical device (e.g., dovetail prism) for causing the inversion of the image and two lenses flanking the optical device. Rotating the optical device causes the irradiation position of light to scan the test subject while altering the measuring position of the transmitted light from the subject. This setup allows the equipment to be manufactured small and inexpensive and enhances the efficiency in utilizing the light from the light source.

According to another aspect of the invention, there is provided an optical CT equipment comprising a plurality of photo detectors for detecting the transmitted light from the subject of the test, the individual photo detectors detecting the transmitted light at each of the measuring positions involved. This setup boosts the efficiency in detection of the transmitted light. The setup also makes it possible to use inexpensive photo detectors each having a relatively narrow dynamic range suitable for the intensity level of the transmitted light at the respective measuring positions of the transmitted light.

The above-mentioned dovetail prism is capable of inverting an optical image transmitted therethrough, as discussed in OPTICS (Eugene Hecht, Alfred Zajac; Addison-Wesley Publishing Company, Inc.; 1974, page 133). When a subject is observed through the dovetail prism, an upside-down image of the subject is visible therethrough. The image thus viewed is axially symmetrical around a straight line which is in parallel with the base plane of the dovetail prism and is perpendicular to the optical axis. Where the dovetail prism is rotated around the optical axis of the incident light, the inverse image obtained through the prism is rotated by twice the angle of the prism rotation. Thus if the dovetail prism is placed and rotated appropriately between two lenses, the inverse image formed by these lenses may be rotated as desired.

Figure 5A:
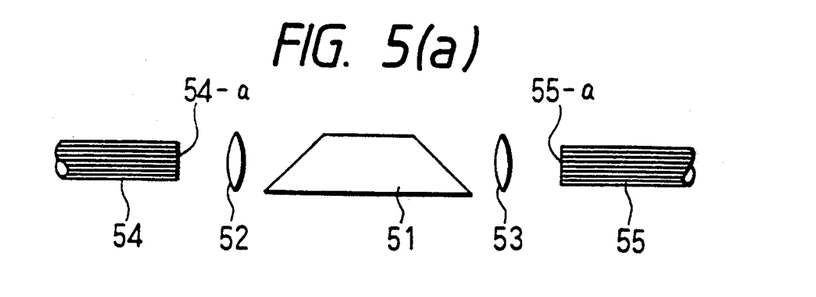

As shown in FIG. 5 (A), the invention envisages the use of an optical system incorporating a dovetail prism 51 between two lenses 52 and 53. The optical plane and the image plane of the optical system correspond to the end face of an optical fiber 54 and that of an optical fiber 55, respectively. That is, the end face 54-a of the optical fiber 54 is located on one focal plane of the lens system including the dovetail prism 51 and the lenses 52 and 53; the end face 55-a of the other optical fiber 55 is located on the other focal plane of the lens system. This setup causes the image at the end face of one optical fiber to be formed inverted at the end face of the other optical fiber.

Figure 5B:
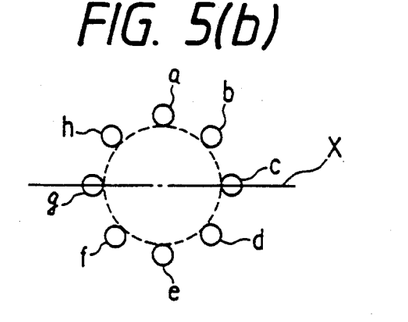
Figure 5C:
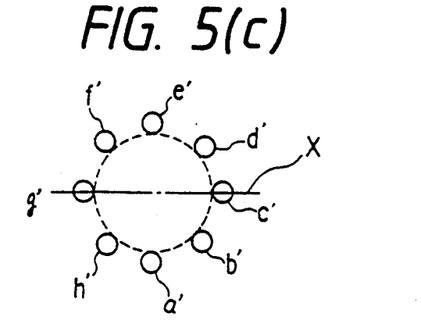

If the threads of the optical fiber 54 at the end face 54-a are arranged as shown in FIG. 5 (B), the inverted images of the individual threads at the end face 55-a of the optical fiber 55 appear as depicted in FIG. 5 (C). Specifically, the images of the threads a, b, c, d, e, f, g and h are formed in the locations a', b', c', d', e', f', g' and h', respectively. Where X represents a line segment which is perpendicular to the optical axis of the optical system and is in parallel with the base plane of the dovetail prism 51, the images of the individual threads are formed in a vertically symmetrical manner about the line segment X. Thus if the threads of the optical fiber 55 at the end face 55-a are located in the thread image positions shown in FIG. 5 (C), the light emitted from the threads of the optical fiber 54 enters the corresponding threads of the optical fiber 55.

When the dovetail prism 51 is rotated, the image formed at the end face of the optical fiber 55 also rotates. Thus suitably rotating the dovetail prism 51 allows the light from the threads of the optical fiber 54 to enter desired threads of the optical fiber 55. That is, rotating the dovetail prism 51 makes it possible to switch the optical connection between the threads of the optical fiber 54 and those of the optical fiber 54.

Although the dovetail prism 51 is used as the optical device for causing image inversion in the description above, this is not limitative of the invention. Alternatively, a suitable combination of plane mirrors may be employed to effect image inversion of the same nature.

Where the optical connection is switched between the optical fibers 54 and 55, the decrease of light intensity lies primarily in the surface reflection by the dovetail prism 51 and by the lenses 52 and 53 on both sides of the prism. However, the reflectance of this surface reflection is as low as a few percent per reflecting surface. This is a significant improvement in terms of light intensity decrease over conventional setups. With the loss of light intensity thus reduced, the efficiency of light transmission between the optical fibers 54 and 55 is boosted considerably.

Where the transmitted light from the test subject is to be detected via the optical fiber 55, each of the fiber threads is connected to an individual photo detector. This arrangement makes it possible to use photo detectors each having a relatively narrow dynamic range suitable for the intensity of the transmitted light per thread.

These and other objects, features and advantages of the invention will become more apparent upon a reading of the following description and appended drawings.

BRIEF DESCRIPTION OF THE DRAWINGS

FIG. 5 (A), FIG. 5 (B) and FIG. 5 (C) are views illustrating the operating principle of the optical scanning method utilizing a dovetail prism according to the invention;

FIG. 9 (A) and FIG. 9 (B) are schematic views showing the constitution of an optical device for image inversion utilizing a reflector arrangement.

BEST MODE FOR CARRYING OUT THE INVENTION

Preferred embodiments of the invention will now be described in detail with reference to the accompanying drawings.

First Embodiment

Figure 1:
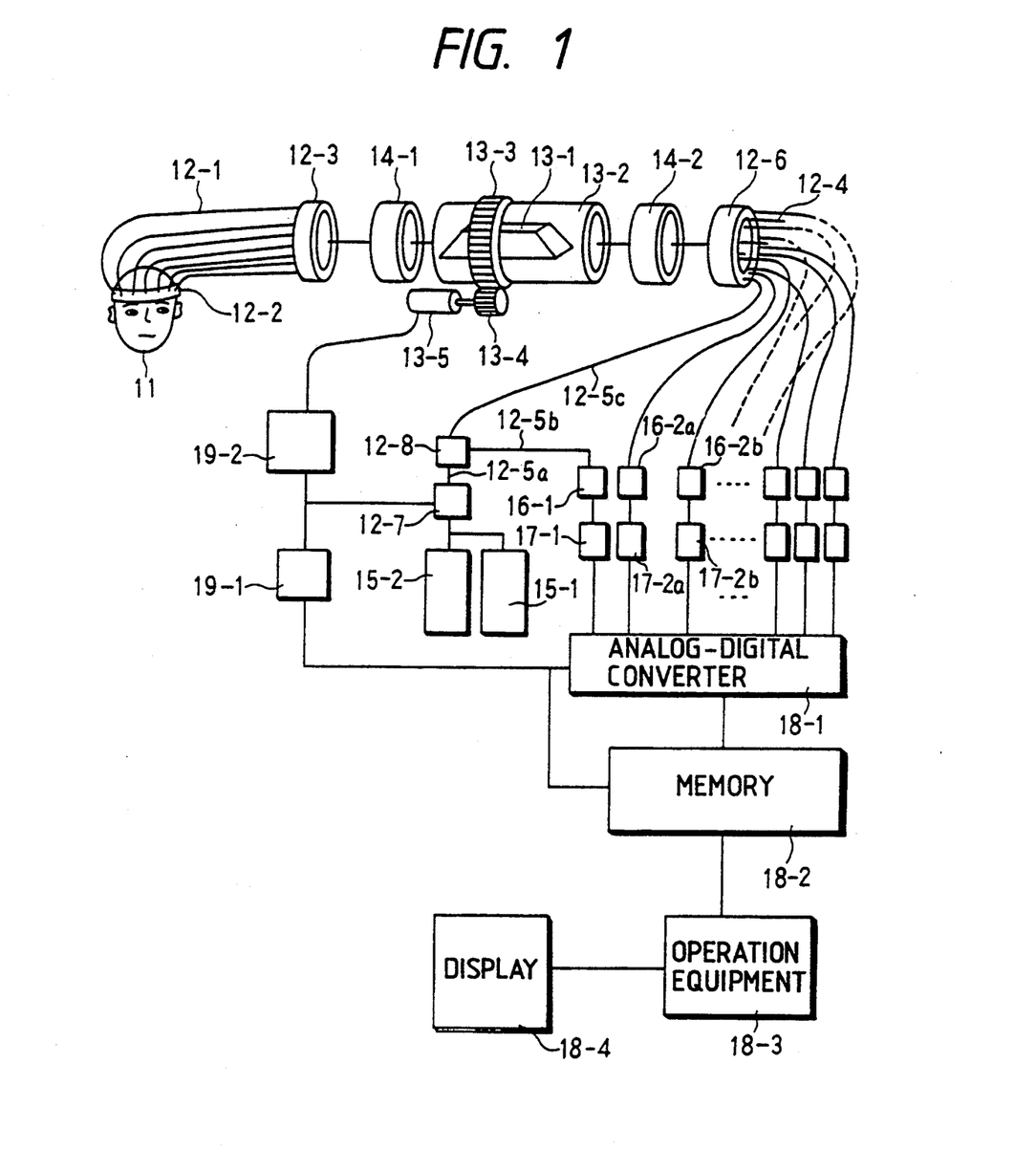
FIG. 1 is a schematic block diagram of optical computed tomography (CT) equipment embodying the invention.

FIG. 1 shows the basic constitution of optical CT equipment practiced as a first embodiment of the invention. Referring to FIG. 1, reference numeral 11 represents a test subject, i.e., the sample whose tomogram is to be observed using the embodiment. An optical fiber 12-1 is composed of numerous threads that guide light toward the test subject 11. An optical fiber holder 12-2 fixes the thread ends at one end face of the fiber 12-1 on the side of the subject 11 under test. Another optical fiber holder 12-3 fixes the thread ends at the other end face of the optical fiber 12-1. The optical fiber holders 12-2 and 12-3 hold the fiber threads in such a manner that at both end faces of the optical fiber 12-1, its thread ends are fixedly arranged along a circumference at equal intervals. A dovetail prism 13-1 is secured in a cylindrical case 13-2. A gear 13-3 is used to rotate the cylindrical case 13-2. A small gear 13-4 transmits the torque of a pulse motor 13-5 to the gear 13-3.

An optical fiber 12-4 also comprises many threads. As with the optical fiber 12-1, the thread ends at one end face of the fiber 12-4 are fixedly positioned along a circumference by an optical fiber holder 12-6. As with the threads of the optical fiber 12-4, each of threads 12-5c has one end thereof secured by the optical fiber holder 12-6. The optical fiber threads 12-5c guide light coming from a light source 15-1 or 15-2. Each of the threads 12-5c has the other end thereof connected to the light sources 15-1 and 15-2 via a beam splitter 12-8 and an optical switch 12-7. The beam splitter 12-8 splits the light coming from the light source 15-1 or 15-2 by way of the optical switch 12-7 and an optical fiber 12-5a. The split light goes through the optical fiber 12-5a to a photo detector (photomultiplier tube) 16-1. The output of the photo detector 16-1 is amplified by an amplifier 17-1. The output of the amplifier 17-1 is used as a monitor signal by which to monitor the intensity of the output light from the light source 15-1 or 15-2. The wavelengths of the output light from the light sources 15-1 and 15-2 are 770 nm and 813 nm, respectively.

Condenser lenses 14-1 and 14-2 have the same focal length. The two lenses are positioned so as to form the image of that end face of the optical fiber 12-1 which is fixed by the optical fiber holder 12-3, onto that end face of the optical fiber 12-4 which is secured by the optical fiber holder 12-6. In like manner, the condenser lenses 14-1 and 14-2 are arranged to form the image of that end face of the optical fiber 12-4 which is fixed by the optical fiber holder 12-6, onto that end face of the optical fiber 12-1 which is secured by the optical fiber holder 12-3.

Photo detectors (photomultiplier tubes) 16-2a, 16-2b, etc. are connected individually to the threads of the optical fiber 12-4. Amplifiers 17-2a, 17-2b, etc. amplify output signals from the photo detectors (photomultiplier tubes) 16-2a, 16-2b, etc. Reference numeral 18-1 stands for an analog-to-digital converter, 18-2 for memory equipment, 18-3 for operation equipment and 18-4 for display equipment.

A clock signal generator 19-1 generates a clock signal that allows the optical switch 12-7, the analog-to-digital converter 18-1, the memory equipment 18-2 and the pulse motor 13-5 to operate in synchronism. A driver circuit 19-2 drives the pulse motor 13-5.

The first embodiment operates as follows: the light from the light sources 15-1 and 15-2 is first guided to the optical switch 12-7 over the optical fiber. The optical switch causes the light from one of the two light sources to enter the optical fiber 12-5a. Having entered the optical fiber 12-5a, the incident light is split by the beam splitter 12-8 in predetermined proportions. One split portion of the light is guided into the optical fiber 12-5b; the other split portion of the light is guided into the optical fiber 12-5c. The light having entered the optical fiber 12-5b is detected by the photo detector 16-1. The output of the photo detector 16-1 is amplified by the amplifier 17-1 and converted from analog to digital format by the analog-to-digital converter 18-1 before being stored in the memory equipment 18-2. The stored data is later used by the operation equipment 18-2 for its operation, the data representing the intensity of the light from the light source. The switching made by the optical switch 12-7 between the two light sources is accomplished in accordance with the clock signal from the clock signal generator 19-1.

What follows is a description of the case in which the optical switch 12-7 is set to guide the light 770 nm in wavelength from the light source 15-1 into the optical fiber 12-5a. Having entered the optical fiber 12-5a, the light 770 nm in wavelength is split by the beam splitter 12-8. One split portion of the light goes through the optical fiber 12-5c up to its end face on the side of the optical fiber holder 12-6. The light is then condensed by the optical system onto the end of one optical fiber thread held by the optical fiber holder 12-3, the optical system comprising the lenses 14-2 and 14-1 as well as the dovetail prism 13-1. Past the optical fiber thread, the light is irradiated to the test subject 11. On receiving the light, the subject 11 transmits it in a scattering manner. The scattered light enters those threads of the optical fiber 12-1 which are fixed by the optical fiber holder 12-1 on the periphery of the test subject 11.

The transmitted light from the subject 11 passes through the threads of the optical fiber 12-1 and is emitted from the thread ends on the side of the optical fiber holder 12-3 toward the lens 14-1. The optical system composed of the lens 14-1, dovetail prism 13-1 and lens 14-2 allows the emitted light to enter those threads of the optical fiber 12-4 which are secured by the optical fiber holder 12-6. Having passed through the threads of the optical fiber 12-4, the light enters the corresponding photo detectors 16-2a, 16-2b, etc. Each of the photo detectors outputs an electrical signal representing the intensity of the light incident on each detector. These output signals are amplified by the amplifiers 17-2a, 17-2b, etc. The amplified signals are converted to digital signals by the analog-to-digital converter 18-1 and stored in the memory equipment 18-2.

Below is a description of the case in which the optical switch 12-7 connects the light source 15-2 instead of the light source 15-1 to the optical fiber 12-5a. In this case, the light 813 nm in wavelength from the light source 15-2 is irradiated to the test subject 11. The processes from the irradiation of light onto the subject 11 up to the storage in the memory equipment 18-2 of the signals representing the intensity of the transmitted light are the same as those of the preceding case in which the light 770 nm in wavelength from the light source 15-1 is irradiated onto the subject 11.

After the operation described above, the pulse motor 13-5 and the gears 13-4 and 13-3 combine to rotate the dovetail prism 13-1. The angle of prism rotation is 180/n degrees, where n represents the number of the threads constituting the optical fiber 12-1. Turning the dovetail prism 13-1 by that angle causes the emitted light from the optical fiber 12-5c to proceed, at the end face of the optical fiber 12-1 on the side of the holder 12-3, into the fiber thread immediately adjacent (in the rotating direction) to the thread on which the light was incident before the prism was rotated. As a result, the irradiation position of light on the subject of the test moves by one thread in the rotating direction of the dovetail prism 13-1 away from the irradiation position in effect before the prism was rotated.

As described, the rotation of the dovetail prism 13-1 by 180/n degrees displaces the optical connection by one thread between the optical fibers 12-1 and 12-4. That is, with the dovetail prism 13-1 rotated, the transmitted light of the subject coming from the optical fiber 12-1 is transmitted to the optical fiber 12-4 after a one-thread displacement in the rotating direction. Before rotation of the dovetail prism 13-1, a particular thread of the optical fiber 12-1 corresponds to a specific thread of the optical fiber 12-4 (for optical transmission); after rotation of the prism, the thread displaced by one thread in the rotating direction away from that particular thread of the optical fiber 12-1 corresponds to that specific thread of the optical fiber 12-4 for optical transmission.

After the irradiation position of light on the test subject is moved by rotation of the dovetail prism 13-1, the initial operation described above is again carried out. This makes it possible successively to measure and store the intensity of the transmitted light from the test subject upon light irradiation from a new irradiation position.

The stepped rotation of the dovetail prism 13-1 is repeated until the irradiation position of light on the test subject 11 has made a complete turn of the periphery of the subject. In this manner, multipoint scanning of the irradiation position is carried out on the test subject 11. The intensity of the transmitted light from the subject is measured in various directions from the respective irradiation positions, and the measurements are stored.

Figure 6:
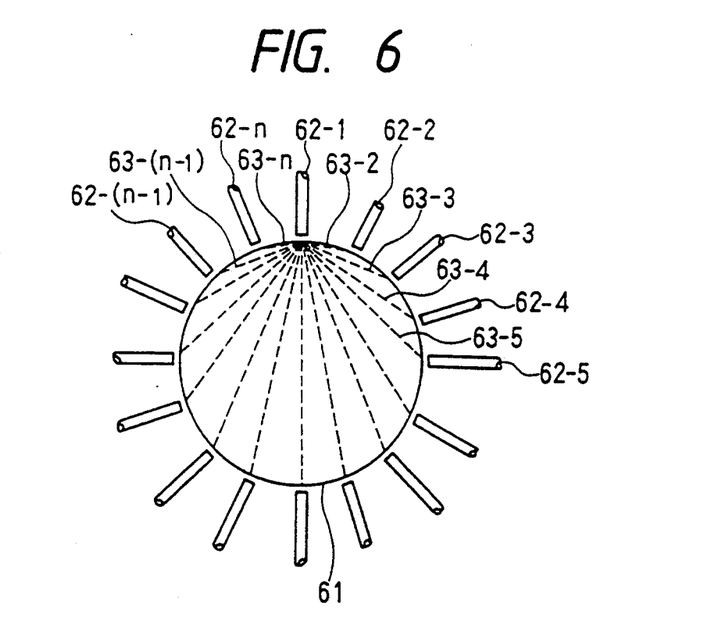
FIG. 6 is a schematic view depicting light paths through a subject of the test.

What follows is a description of how the data thus measured and stored is processed. FIG. 6 shows how optical fiber threads are typically arranged along the periphery of the subject in the setup of FIG. 1. In FIG. 6, reference numeral 61 represents the test subject. Optical fiber threads 62-1, 62-2, . . . , 62-n are arranged so that their ends come in contact with the subject along the periphery thereof. Straight lines 63-2, 63-3, . . . , 63-n connect the point of irradiation by the optical fiber thread 62-1 to the measuring points of the transmitted light entering the optical fiber threads 62-2, 62-3, . . . , 62-n.

Suppose that the optical fiber thread 62-1 now irradiates light to the test subject 61. In that case, the light transmitted to the measuring point of the optical fiber thread 62-5 is considered to pass substantially close to the straight line 63-5. The intensity of the light having passed along the straight line 63-5 to enter the optical fiber thread 62-5 decays due to absorption and scattering inside the subject. Thus measuring that intensity of the transmitted light reveals the decrease rate thereof along the straight line 63-5.

However, given only the measurement of the transmittance of the light having one wavelength, it is impossible to tell whether the decay is due to scattering or to absorption. To obtain the decrease rate attributable only to absorption requires measuring two kinds of light having two different wavelengths. The two kinds of light are measured for transmittance and the measurements are used to calculate the decrease rate resulting solely from absorption.

The wavelengths of the light to be measured are set at 770 nm and 813 nm. The reason for this is that when the test subject is a human body, the light 770 nm in wavelength is absorbed greatly by the hemoglobin contained in the blood whereas the light having a wavelength of 813 nm is hardly absorbed thereby. Because the light 813 nm in wavelength is not much absorbed by the hemoglobin, the decay of the light is mostly attributable to scattering. On the other hand, the light 770 nm in wavelength decays because of both absorption and scattering as it passes through the human body. Therefore, subtracting the decrease rate of the light 813 nm in wavelength from that of the light 770 nm in wavelength provides the decrease rate due only to the absorption by the hemoglobin.

In this manner, the intensities of the transmitted light of two different wavelengths are measured, and these measurements are used to find the decrease rate of the transmitted light due to absorption in diverse directions from a given irradiation position on the test subject. The data about the absorption-induced decrease of the transmitted light in various directions from a given irradiation position constitutes projection data about that irradiation position.

The dovetail prism is rotated in stepping fashion, i.e., by a small angle at a time, until the irradiation position has made a complete turn on the periphery of the subject under test. Projection data is acquired in each of the irradiation positions. The projection data thus obtained is stored in the memory equipment 18-2.

A tomogram of the test subject is composed as follows: the projection data about a given irradiation position is subjected to Fourier transformation. A separately provided filter function is operated on the transformed data. The resulting data is then subjected to inverse Fourier transformation. These operations are carried out on the data of all irradiation positions involved. The data following inverse Fourier transformation is superposed on that position inside the subject which is determined by both the irradiation position and the measuring position of the transmitted light. This composes a two-dimensional image (tomogram) of the target position in the test subject. This process of composing tomogram is known as the back projection method. The method is discussed in more detail in "Image Reconstruction from Projection (T. Herman; Academic Press)." The operations involved are performed by the operation equipment 18-3 based on the data stored in the memory equipment 18-2. The composed tomogram of the target is displayed on the display equipment 18-4.

Second Embodiment

The second embodiment is improved optical CT equipment that eliminates the fluctuation in the efficiency of transmitting light between optical fibers. The basic constitution of the second embodiment is the same as that of the first embodiment (FIG. 1). The difference is that different diameters are determined for the cores of the threads in the optical fibers used.

With the second embodiment, the threads constituting the optical fiber 12-1 have a core diameter of 0.5 mm each, and the threads making up the optical fiber 12-4 have a core diameter of 3.0 mm each. The optical fiber 12-5c has a core diameter of 0.125 mm for its threads.

The transmission of light between optical fibers is accomplished by way of a lens arrangement. For example, the light guided from the light source 15-1 over the optical fiber 12-5c passes through the lens 14-2 and enters the dovetail prism 13-1. After transmission through the prism, the light is focused by the lens 14-1 onto the end face of the optical fiber 12-1. This causes an end face image of the optical fiber 12-5c to be formed at the end face of the optical fiber 12-1. The size (i.e., diameter) of this image is 0.125 mm, the same as the core diameter of the optical fiber 12-5c. This is because the focal length of the lens 14-1 is the same as that of the lens 14-2. If the image size is greater than the core diameter of the threads constituting the optical fiber 12-1, not all light from the optical fiber 12-5c can enter each of the threads of the optical fiber 12-1. The partial loss of the light translates into a decrease in the intensity of the light irradiated to the subject of the test. Where the image size is the same as the core diameter of each of the threads in the optical fiber 12-1, a light loss can still occur as a result of the image forming position being dislocated from the corresponding thread of the optical fiber 12-1 following a slight change in the rotation angle of the dovetail prism. In this respect, the second embodiment sets the core diameter of 0.5 mm for each thread in the optical fiber 12-1, the core diameter being sufficiently greater than the size of the end face image of the optical fiber 12-5c (0.125 mm in diameter). Thus a slight displacement of the image forming position does not prevent all light from the optical fiber 12-5c from entering the corresponding thread of the optical fiber 12-1.

The same holds true when the transmitted light from the test subject (sample) is moved from the optical fiber 12-1 to the optical fiber 12-4. Specifically, the second embodiment sets the core diameter of as large as 3 mm for each of the threads of the optical fiber 12-4, compared with the diameter of 0.5 mm for the image formed at the thread end face of the optical fiber 12-1. The different core diameters make it possible for the transmitted light from the test subject past a given thread of the optical fiber 12-1 to fully enter the corresponding thread of the optical fiber 12-4. The light eventually reaches the corresponding photo detector for detection.

As described, the second embodiment uses three different core diameters: the core diameter of the optical fiber thread 12-5c for guiding the light from the light source 15-1 or 15-2 to the lens 14-2 is smaller than the core diameter of each of the threads of the optical fiber 12-1 for guiding the light from the lens 14-1 to the surface of the subject under test. Then the core diameter of each of the threads making up the optical fiber 12-1 for guiding the transmitted light from the subject to the lens 14-1 is smaller than the core diameter of the threads in the optical fiber 12-4 for guiding the transmitted light from the lens 14-2 to the photo detectors 16-2a, 16-2b, etc. Even if the stopped position of the dovetail prism 13-1 after rotation is slightly dislocated from the exact position, the efficiency of light transmission between the optical fiber threads is not adversely affected. Thus the second embodiment drastically reduces dispersion of measured data and provides tomogram of high repeatability.

Third Embodiment

Figure 7:
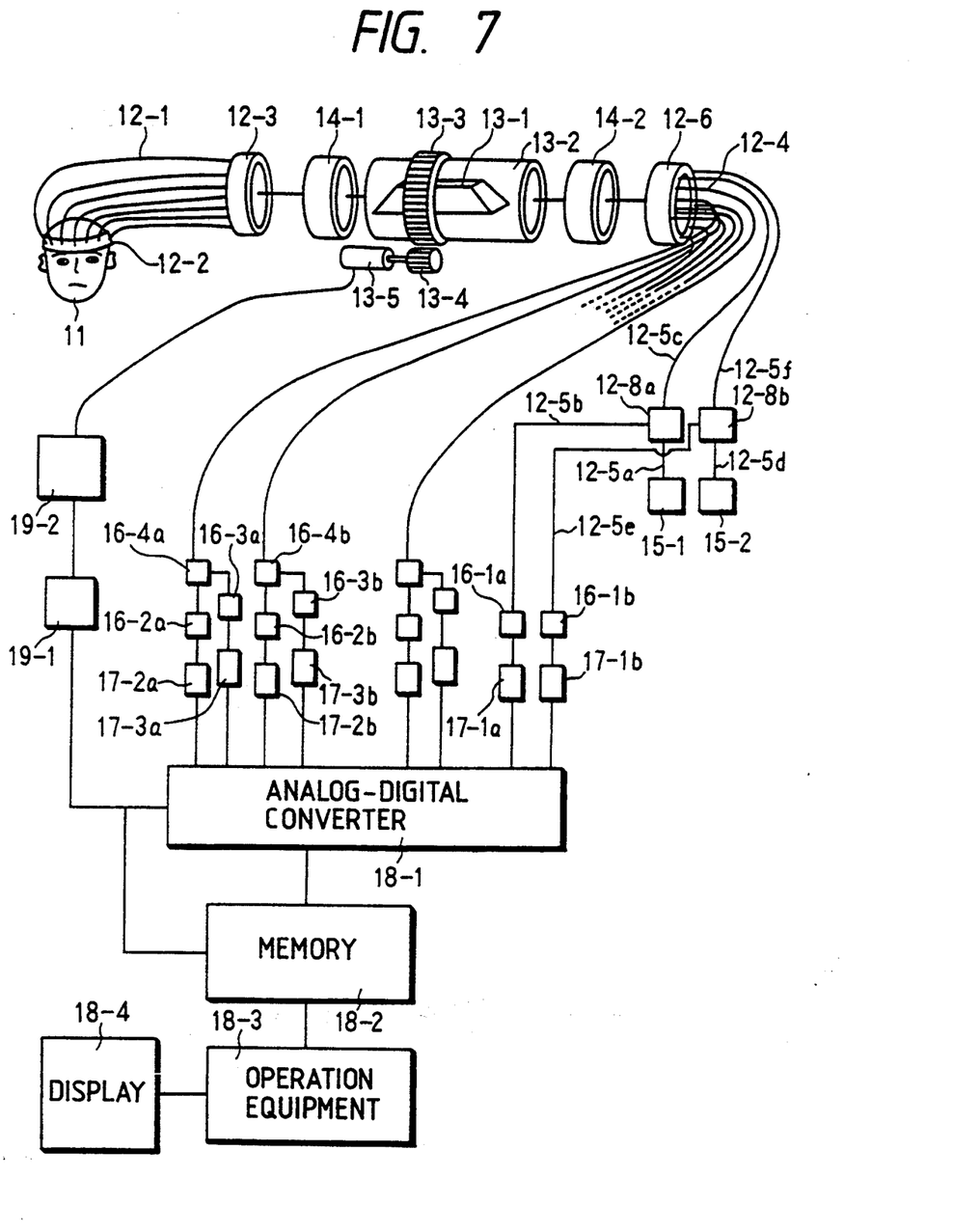
FIG. 7 is a schematic block diagram of another optical CT equipment embodying the invention.

FIG. 7 depicts the basic constitution of another optical CT equipment practiced as a third embodiment of the invention. The third embodiment differs from the first embodiment in the way that light is irradiated to the test subject. With the first embodiment, the optical switch 12-8 selects one of the light sources 15-1 and 15-2 for alternate irradiation of the light having a different wavelength onto the subject under test. By contrast, the third embodiment involves simultaneously irradiating onto the subject two kinds of light having two different wavelengths from two light sources.

The light from the light source 15-1 is transmitted to a beam splitter 12-8a. The beam splitter 12-8a splits the light into two portions: one portion for transmission to an optical fiber 12-5b, the other portion for transmission to an optical fiber 12-5c. The light branched to the optical fiber 12-5b is sent to and detected by a photo detector 16-1a. The output signal of the photo detector 16-1a is amplified by an amplifier 17-1a and converted to a digital signal by an analog-to-digital converter 18-1. After conversion, the digital signal is stored in memory equipment 18-2. The stored signal is later used during operation by the operation equipment 18-3 as a signal representing the intensity of the light from the light source 15-1 irradiated to the test subject 11.

Meanwhile, the light branched to the optical fiber 12-5c passes therethrough to reach the fiber end face on the side of the optical fiber holder 12-6. Thereafter, the light goes through the same optical paths as in the first embodiment and is irradiated to the subject 11 of the test.

As with the output light from the light source 15-1, the output light from the light source 15-2 is conveyed by an optical fiber 12-5d to a beam splitter 12-8b. The beam splitter 12-8b splits the received light in two in predetermined proportions. One split portion of the light is sent through an optical fiber 12-5e to a photo detector 16-1b for detection thereby. The detection signal from the photo detector 16-1b is amplified by an amplifier 17-1b and converted to a digital signal by the analog-to-digital converter 18-1. The digital signal is stored in the memory equipment 18-2. The other split portion of the light is sent via an optical fiber 12-5f to the fiber end face on the side of the optical fiber holder 12-6. Thereafter, the light goes through the same optical paths as in the first embodiment and is irradiated to the test subject 11.

In the manner described, two kinds of light with two different wavelengths from the two light sources 15-1 and 15-2 are irradiated simultaneously to the test subject 11. As with the first embodiment, the transmitted light from the subject 11 is sent from the optical fiber 12-1 to the optical fiber 12-4.

Having entered the threads of the optical fiber 12-4, two kinds of the transmitted light having two different wavelengths are separated in terms of wavelength by dichroic prisms 16-4a, 16-4b, etc. For example, the dichroic prism 16-4a separates the light with a first wavelength from the light source 15-1, from the light with a second wavelength from the light source 15-2. The first-wavelength light from the light source 15-1 is sent to the photo detector 16-2a, and the second-wavelength light from the light source 15-2 is transmitted to a photo detector 16-3a. The detection signals from the photo detectors 16-2a and 16-3a are amplified by amplifiers 17-2a and 17-3a, respectively, before being sent to the analog-to-digital converter 18-1. Likewise, the dichroic prism 16-4b separates the two kinds of the transmitted light having two different wavelengths. One separated light portion having one wavelength is detected by the photo detector 16-2b, and the other light portion having the other wavelength, by the photo detector 16-3b. The detection signals from the photo detectors 16-2b and 16-3b are amplified by amplifiers 17-2b and 17-3b, respectively, before being sent to the analog-to-digital converter 18-1. The transmitted light from the subject 11 having entered the other threads of the optical fiber 12-4 is similarly separated in terms of wavelength. The respective detection signals are amplified and sent to the analog-to-digital converter 18-1.

As described, the third embodiment has two kinds of light with two different wavelengths irradiated simultaneously to the test subject 11. The embodiment also carries out simultaneous detection of the two kinds of the transmitted light from the subject 11 with two different wavelengths.

The third embodiment is the same as the first embodiment in such processes as rotating the dovetail prism 13-1 for scanning the subject 11 with the irradiation position of light, storing signals from the analog-to-digital converter 18-1 into the memory equipment 18-2, utilizing the stored data for operation by the operation equipment 18-3 to compose tomogram of the subject 11, and displaying the composed tomogram of the subject 11 on the display equipment 18-4.

Because the third embodiment makes it possible to measure the subject of the test by simultaneously using two kinds of light with two different wavelengths, the measuring time is shortened significantly. This feature is convenient where the internal condition of the subject to be tested keeps changing over time.

Fourth Embodiment

Figure 8:
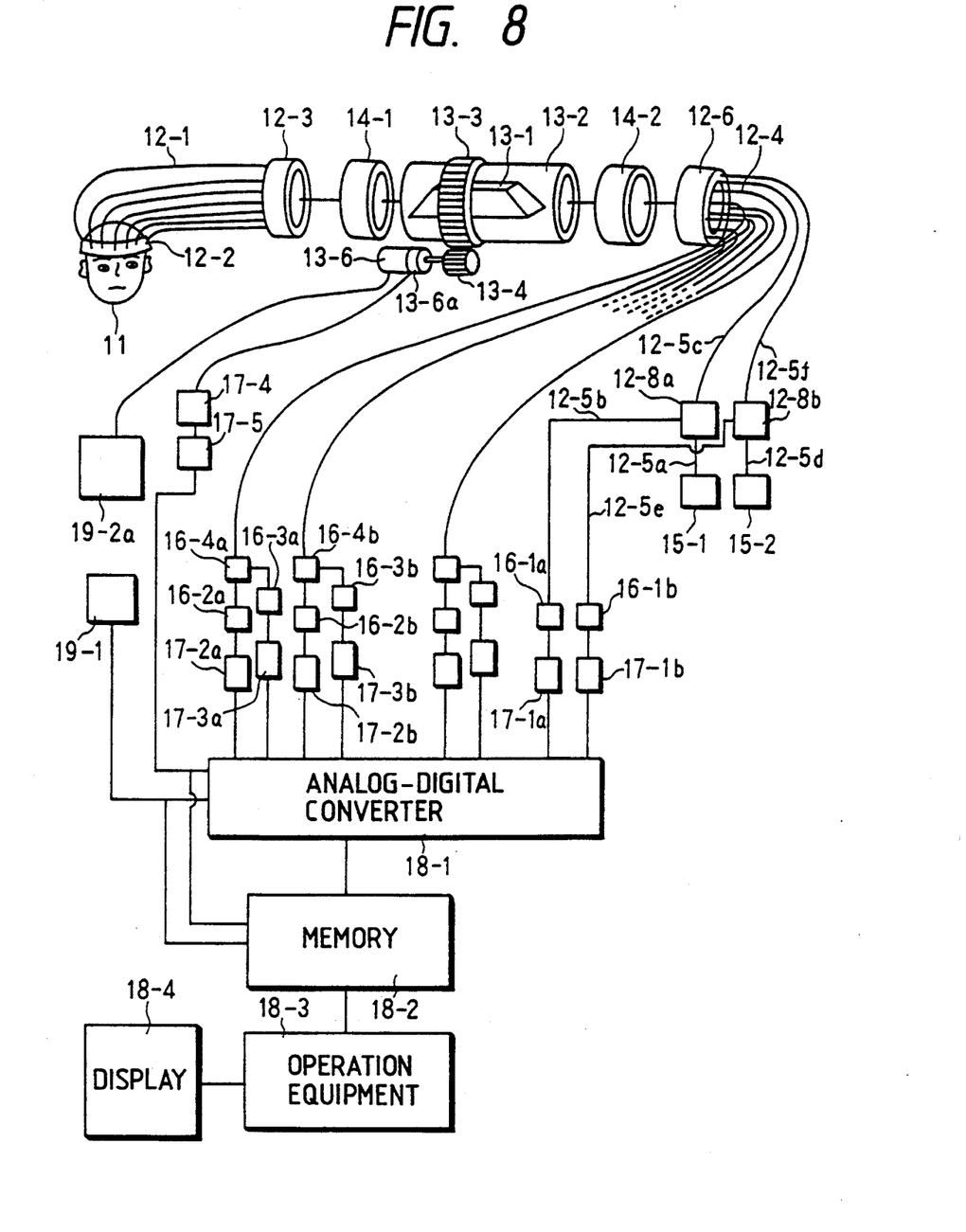
FIG. 8 is a schematic block diagram of another optical CT equipment embodying the invention.

FIG. 8 shows the basic constitution of another optical CT equipment practiced as a fourth embodiment of the invention. The fourth embodiment is a version of the third embodiment wherein the pulse motor 13-5 for rotating the dovetail prism 13-1 is replaced by a direct current motor 13-6. The direct current motor 13-6 is driven by a direct current source 19-2a. The rotation angle of the direct current motor 13-6 is detected by a rotary encoder 13-6a. The output signal of the rotary encoder 13-6a representing the detected rotation angle is converted to a digital signal by an analog-to-digital converter 17-4. After conversion, the digital signal is sent to a frequency divider 17-5. Given the rotation angle signal from the analog-to-digital converter 17-4, the frequency divider 17-5 generates one pulse signal for every 180/n degrees of the rotation of the dovetail prism 13-1. Character n represents the number of those threads of the optical fiber 12-1 which are held fixedly by the optical fiber holder 12-3.

In its mechanism, the fourth embodiment has the direct current motor 13-6 driven to rotate the dovetail prism 13-1 by way of a torque transmission mechanism comprising gears 13-4 and 13-3. The turning of the dovetail prism 13-1 entails the rotation of an image of the end face of the optical fiber 12-1 on the side of the fiber holder 12-3, the rotated image being formed at the end face of the optical fiber 12-4 on the side of the fiber holder 12-6 by use of the image inverting optical system comprising the lens 14-1, dovetail prism 13-1 and lens 14-2. Every time the dovetail prism 13-1 rotates by 180/n degrees, the end face images of the threads of the optical fiber 12-1 formed at the end face of the optical fiber 12-4 on the side of the fiber holder 12-6 overlap with the end faces of the threads of the optical fiber 12-4. At this point, the light from the light sources 15-1 and 15-2 is irradiated to the test subject 11. The transmitted light from the subject 11 is transmitted to the threads of the optical fiber 12-4. Having entered the threads of the optical fiber 12-4, the transmitted light is separated in terms of wavelength by the dichroic prisms 16-4a, 16-4b, etc. The separated light portions with different wavelengths are detected by two groups of photo detectors: one group comprising photo detectors 16-2a, 16-2b, etc., the other group including photo detectors 16-3a, 16-3b, etc. The detection signals from the photo detectors are amplified by the amplifiers 17-2a, 17-2b, etc. as well as by the amplifiers 17-3a, 17-3b, etc. before being sent to the analog-to-digital converter 18-1.

In the above state, the frequency divider 17-5 generates a pulse signal based on the rotation angle signal from the encoder 13-6a. The pulse signal is transmitted to the analog-to-digital converter 18-1 and to the memory equipment 18-3. Every time it receives a pulse signal, the analog-to-digital converter 18-1 carries out its analog-to-digital conversion operation anew. The memory equipment 18-2 collects data in synchronism with the pulse signal.

As the dovetail prism 13-1 is rotated by the direct current motor 13-6, the end face image of the optical fiber 12-3 formed at the end face of the optical fiber 12-4 is also rotated. The end face of each thread in the optical fiber 12-4 overlaps with the end face image of a different thread in the optical fiber 12-3. That is, as the irradiation position of light on the test subject 11 changes consecutively, the intensity of the transmitted light from the subject 11 is measured repeatedly in different irradiation positions. The projection data about the test subject 11 is thus measured and acquired. Calculations are made based on the projection data to compose the tomogram of the subject 11.

Fifth Embodiment

In the embodiments described so far, the dovetail prism for image inversion may be replaced by a combination of plane mirrors constituting an optical device for executing image inversion of the same nature. The fifth embodiment of the invention is an image inverting optical device that combines plane mirrors.

Figure 9A:
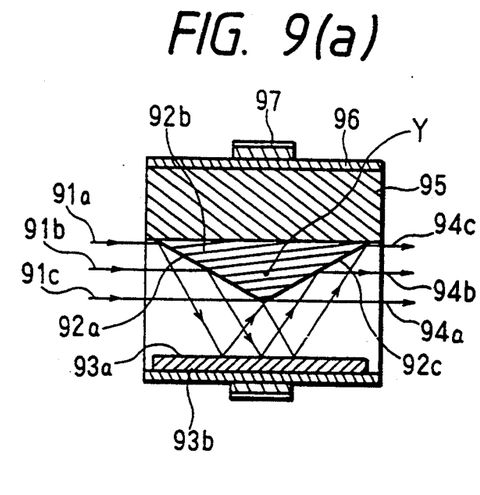
Figure 9B:
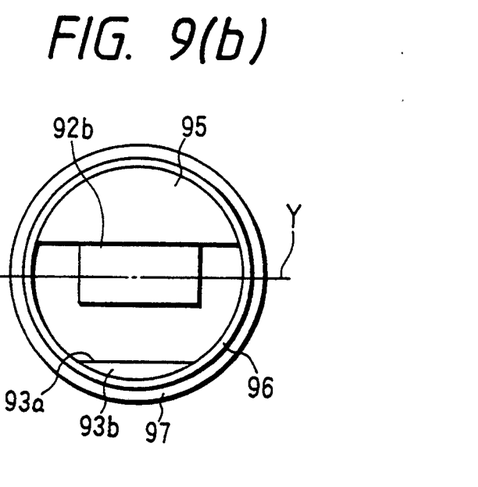

FIGS. 9 (A) and 9 (B) depict the structure of an optical device comprising plane mirrors for providing the function equivalent to that of the dovetail prism. The optical device includes a first reflection surface 92a, a second reflection surface 93a and a third reflection surface 92c. The first reflection surface 92a and third reflection surface 92c are two surfaces of a glass prism, each surface having a thin aluminum film deposited thereon for light reflecting purposes. The second reflection surface 93a is constructed by depositing a light-reflecting thin aluminum film on the surface of a glass reflector 93b. The prism 92b is fixedly attached to the inside of a cylinder 96 by use of a holder 95. The reflector 93b is secured directly to the inside of the cylinder 96. The holder 95 is positioned so that the center position of the prism 92b comes immediately on the center axis of the cylinder 96. (The center position of the prism 92b is the position that bisects the distance between the prism bottom in contact with the holder 95 on the one hand, and the line of intersection formed between the first reflection surface 92a and the third reflection surface 92c on the other.) The outer circumference of the cylinder 96 is furnished with a gear 97 that serves to rotate the cylinder 96.

Incident light beams 91a, 91b and 91c on this optical device are reflected by the second reflection surface 93a. The reflection vertically inverts the light beams in an axially symmetrical manner around a line segment Y drawn at the center of the prism 92b. After inversion, the incident light beams come out as emitted light beams 94a, 94b and 94c. As illustrated, the highest incident light beam 91a comes out as the lowest emitted light beam 94a; conversely, the lowest incident light beam 91c comes out as the highest emitted light beam 94c. Thus the optical image incident on this optical device comes out as an image inverted vertically and axially around the line segment Y.

As described, the image inverting optical device combining plane mirrors as shown in FIGS. 9 (A) and 9 (B) provides the same image inverting function as the dovetail prism in the preceding embodiments. Turning this optical device causes the inverted image coming out therefrom to rotate by twice the angle of the device rotation. Thus the image inverting optical device depicted in FIGS. 9 (A) and 9 (B) replaces the dovetail prism in the first through the fourth embodiments and still ensures the same effects as those offered by these preceding embodiments.

As described and according to the invention, the high velocity at which to scan the subject of the test with light shortens the time required to take measurements. Whereas a prolonged measuring time can let the internal condition of the subject under test be altered during measurement, the invention makes it possible to complete the measurement before the condition of the subject changes. This feature ensures more accurate tomography of the test subject.

Another benefit of the invention is its economy. The invention has no need for expensive photo detectors having a wide dynamic range for measurement, relying instead on cheap photo detectors with lesser performance. This is a significant economic advantage. The intensity of the transmitted light from the test subject varies considerably depending on the distance traveled by the light inside the subject. It follows that the intensity of the transmitted light beam from the subject entering the optical fiber varies appreciably from one thread thereof to another. If a single photo detector were to measure the intensity of the transmitted light over all optical fiber threads, the dynamic range of the detector would have to be quite extensive. This is where the invention proves advantageous as it reports to the use of individual photo detectors for measuring the intensity of the transmitted light over individual threads of the optical fiber 12-4. When a given thread of the optical fiber 12-4 is considered, the intensity of the transmitted light from the subject entering that thread changes only within a limited range. The individual photo detector connected to that one thread of the optical fiber need not have a wide dynamic range for measurement; the measuring level of the detector need only be adjusted in keeping with the intensity level of the incident light. With the need for the expensive photo detector eliminated, the equipment according to the invention is manufactured economically.

As many apparently different embodiments of this invention may be made without departing from the spirit and scope thereof, it is to be understood that the invention is not limited to the specific embodiments thereof except as defined in the appended claims.

We claim:

1. Optical computed tomography equipment comprising:

light irradiating means for irradiating light to a subject under test from a plurality of positions along the periphery of said subject;

light detecting means for detecting the intensity of the light transmitted from said subject in a plurality of positions along the periphery of said subject;

data processing means for finding through computation the two-dimensional distribution of a target object inside said subject based on that intensity of the transmitted light from said subject which is detected by said light detecting means, on that position of said subject to which said light irradiating means irradiates light, and on the position in which said light detecting means detects the intensity of the transmitted light; and image display means for displaying in the form of an image said two-dimensional distribution of said target object obtained by said data processing means;

wherein said light irradiating means includes a light source for emitting a span of light ranging from visible to near infrared light; an image inverting optical device for inverting an incident light image in an axially symmetrical manner for output; light incidence means for causing the emitted light from said light source to enter said image inverting optical device; a plurality of first optical fiber threads for guiding the emitted light from said image inverting optical device to the light irradiated positions along the periphery of said subject; and rotating means for rotating said image inverting optical device around the optical axis thereof.

2. Optical computed tomography equipment according to claim 1, wherein said image inverting optical device is a dovetail prism.

3. Optical computed tomography equipment according to claim 1, wherein said image inverting optical device comprises a combination of plane mirrors.

4. Optical computed tomography equipment according to claim 1, wherein said light source includes a minimum of two light sources having different output light wavelengths.

5. Optical computed tomography equipment according to claim 4, wherein said light irradiating means alternately selects one of said minimum of two light sources for incidence of the light therefrom onto said image inverting optical device.

6. Optical computed tomography equipment according to claim 4, wherein said light irradiating means causes the output light from said minimum of two light sources simultaneously to enter said image inverting optical device.

7. Optical computed tomography equipment according to claim 1, wherein said light incidence means includes a plurality of second optical fiber threads for guiding the light from said light source to said image inverting optical device, the core diameter of said second optical fiber threads being smaller than the core diameter of said first optical fiber threads.

8. Optical computed tomography equipment according to claim 1, wherein said light detecting means includes a plurality of third optical fiber threads positioned where an end face image of said first optical fiber threads is formed via said image inverting optical device, and a plurality of photo detectors connected respectively to said third optical fiber threads.

9. Optical computed tomography equipment according to claim 8, wherein the core diameter of said third optical fiber threads is greater than the core diameter of said first optical fiber threads.

* * * * *